United States Patent
Wingo

(10) Patent No.: US 6,398,127 B1
(45) Date of Patent: Jun. 4, 2002

(54) SCENT DISPENSING DEVICE FOR USE IN A CLOTHES DRYER

(76) Inventor: Dora Wingo, 3075 Steve Rd., Wauchula, FL (US) 33873-4521

( * ) Notice: Subject to any disclaimer, the term of this patent is extended or adjusted under 35 U.S.C. 154(b) by 0 days.

(21) Appl. No.: 09/675,186

(22) Filed: Sep. 29, 2000

(51) Int. Cl.⁷ .............................. A24F 25/00; A61L 9/04
(52) U.S. Cl. .............................. 239/55; 239/53; 239/56; 239/57
(58) Field of Search .............................. 239/53, 55, 56, 239/57, 58; 510/519, 520; 34/60, 90, 346

(56) References Cited

U.S. PATENT DOCUMENTS

| | | | |
|---|---|---|---|
| 2,738,225 A | * 3/1956 | Meek | ............................ 239/55 |
| 4,014,105 A | * 3/1977 | Furgal et al. | .................... 34/12 |
| 4,374,571 A | 2/1983 | Hirvela | |
| 4,532,722 A | * 8/1985 | Sax | ................................ 34/60 |
| D286,323 S | 10/1986 | Haworth | |
| 5,072,526 A | 12/1991 | Hirota et al. | |
| 5,384,186 A | * 1/1995 | Trinh | .......................... 428/240 |
| 5,431,879 A | 7/1995 | Heyl et al. | |
| 5,857,281 A | 1/1999 | Bergquist et al. | |
| 5,875,968 A | 3/1999 | Miller et al. | |
| 6,010,540 A | * 1/2000 | Telesca et al. | .................. 8/142 |
| 6,143,713 A | * 11/2000 | Littig et al. | .................. 510/520 |

* cited by examiner

*Primary Examiner*—William C. Doerrler
*Assistant Examiner*—Davis Hwu

(57) ABSTRACT

A scent dispensing device for use in a clothes dryer for transferring a scent onto clothes in a clothes dryer. The scent dispensing device for use in a clothes dryer includes a cylinder. The cylinder has a bottom wall. A peripheral wall is integrally coupled to and extends upwardly from a peripheral edge of the bottom wall. The peripheral wall has a plurality of apertures therein. A cap member has a top wall. A perimeter wall is integrally coupled to and extends downwardly from the top wall for positioning over a top edge of the cylinder. Each of a plurality of panels comprises an absorbent material. A scented fluid is positioned on the panels and one of the panels is positioned in the cylinder.

5 Claims, 3 Drawing Sheets

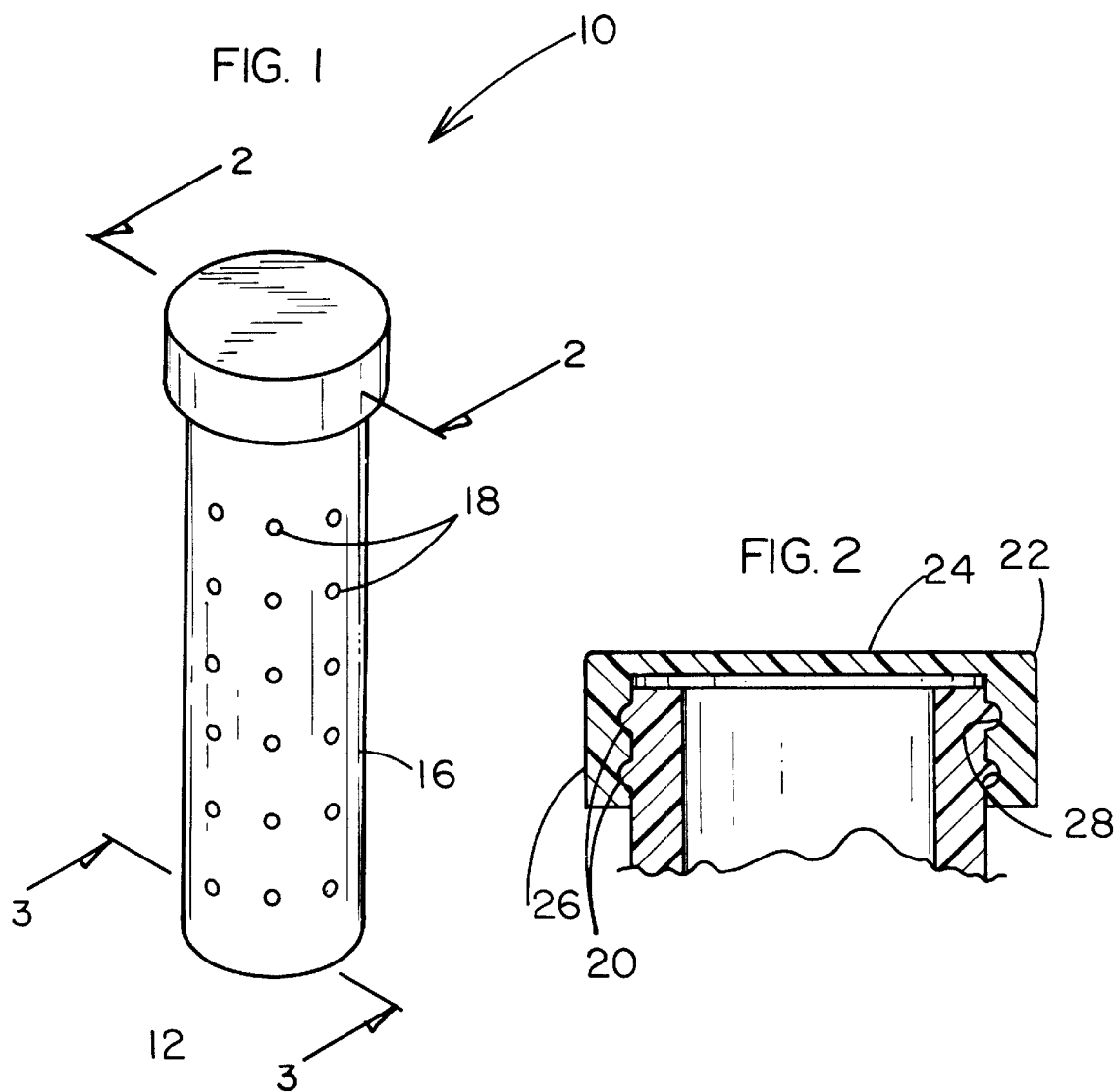

SCENT DISPENSING DEVICE FOR USE IN A CLOTHES DRYER

BACKGROUND OF THE INVENTION

1. Field of the Invention

The present invention relates to scent dispensing devices and more particularly pertains to a new scent dispensing device for use in a clothes dryer for transferring a scent onto clothes in a clothes dryer.

2. Description of the Prior Art

The use of scent dispensing devices is known in the prior art. More specifically, scent dispensing devices heretofore devised and utilized are known to consist basically of familiar, expected and designs encompassed by the crowded prior art which have been developed for the fulfillment of countless objectives and requirements.

Known prior art includes U.S. Pat. No. 4,374,571; U.S. Pat. No. 5,431,879; U.S. Pat. No. 5,079,526; U.S. Pat. No. 5,857,281; U.S. Pat. No. 5,875,968; and U.S. Des. Pat. No. 286,323.

While these devices fulfill their respective, particular objectives and requirements, the aforementioned patents do not disclose a new scent dispensing device for use in a clothes dryer. The inventive device includes a cylinder. The cylinder has a bottom wall. A peripheral wall is integrally coupled to and extends upwardly from a peripheral edge of the bottom wall. The peripheral wall has a plurality of apertures therein. A cap member has a top wall. A perimeter wall is integrally coupled to and extends downwardly from the top wall for positioning over a top edge of the cylinder. Each of a plurality of panels comprises an absorbent material. A scented fluid is positioned on the panels and one of the panels is positioned in the cylinder.

In these respects, the scent dispensing device for use in a clothes dryer according to the present invention substantially departs from the conventional concepts and designs of the prior art, and in so doing provides an apparatus primarily developed for the purpose of transferring a scent onto clothes in a clothes dryer.

SUMMARY OF THE INVENTION

In view of the foregoing disadvantages inherent in the known types of scent dispensing devices now present in the prior art, the present invention provides a new scent dispensing device for use in a clothes dryer construction wherein the same can be utilized for transferring a scent onto clothes in a clothes dryer.

The general purpose of the present invention, which will be described subsequently in greater detail, is to provide a new scent dispensing device for use in a clothes dryer apparatus and method which has many of the advantages of the scent dispensing devices mentioned heretofore and many novel features that result in a new scent dispensing device for use in a clothes dryer which is not anticipated, rendered obvious, suggested, or even implied by any of the prior art scent dispensing devices, either alone or in any combination thereof.

To attain this, the present invention generally comprises a cylinder. The cylinder has a bottom wall. A peripheral wall is integrally coupled to and extends upwardly from a peripheral edge of the bottom wall. The peripheral wall has a plurality of apertures therein. A cap member has a top wall. A perimeter wall is integrally coupled to and extends downwardly from the top wall for positioning over a top edge of the cylinder. Each of a plurality of panels comprises an absorbent material. A scented fluid is positioned on the panels and one of the panels is positioned in the cylinder.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new scent dispensing device for use in a clothes dryer apparatus and method which has many of the advantages of the scent dispensing devices mentioned heretofore and many novel features that result in a new scent dispensing device for use in a clothes dryer which is not anticipated, rendered obvious, suggested, or even implied by any of the prior art scent dispensing devices, either alone or in any combination thereof.

It is another object of the present invention to provide a new scent dispensing device for use in a clothes dryer which may be easily and efficiently manufactured and marketed.

It is a further object of the present invention to provide a new scent dispensing device for use in a clothes dryer which is of a durable and reliable construction.

An even further object of the present invention is to provide a new scent dispensing device for use in a clothes dryer which is susceptible of a low cost of manufacture with regard to both materials and labor, and which accordingly is then susceptible of low prices of sale to the consuming public, thereby making such scent dispensing device for use in a clothes dryer economically available to the buying public.

Still yet another object of the present invention is to provide a new scent dispensing device for use in a clothes dryer which provides in the apparatuses and methods of the prior art some of the advantages thereof, while simultaneously overcoming some of the disadvantages normally associated therewith.

Still another object of the present invention is to provide a new scent dispensing device for use in a clothes dryer for transferring a scent onto clothes in a clothes dryer.

Yet another object of the present invention is to provide a new scent dispensing device for use in a clothes dryer which includes a cylinder. The cylinder has a bottom wall. A peripheral wall is integrally coupled to and extends upwardly from a peripheral edge of the bottom wall. The peripheral wall has a plurality of apertures therein. A cap member has a top wall. A perimeter wall is integrally coupled to and extends downwardly from the top wall for positioning over a top edge of the cylinder. Each of a plurality of panels comprises an absorbent material. A scented fluid is positioned on the panels and one of the panels is positioned in the cylinder.

Still yet another object of the present invention is to provide a new scent dispensing device for use in a clothes dryer that allows a user to place a scent displacing device into a clothes drying having their choice of scents placed on either crystals or preferated panels. The user places their own perfumes and other scents directly on the absorbent materials.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of the first embodiment of a new scent dispensing device for use in a clothes dryer according to the present invention.

FIG. 2 is a schematic cross-sectional view taken along line 2—2 of the present invention.

DESCRIPTION OF THE PREFERRED EMBODIMENT

Figure 3:
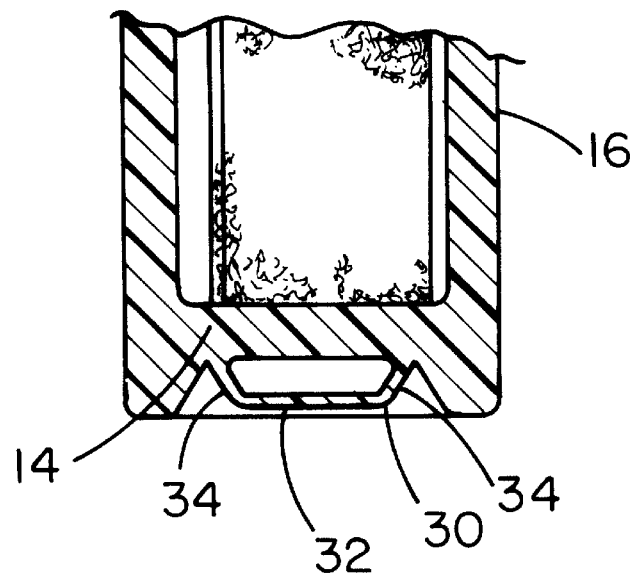
FIG. 3 is a schematic cross-sectional view taken along line 3—3 of the present invention.
Figure 4:
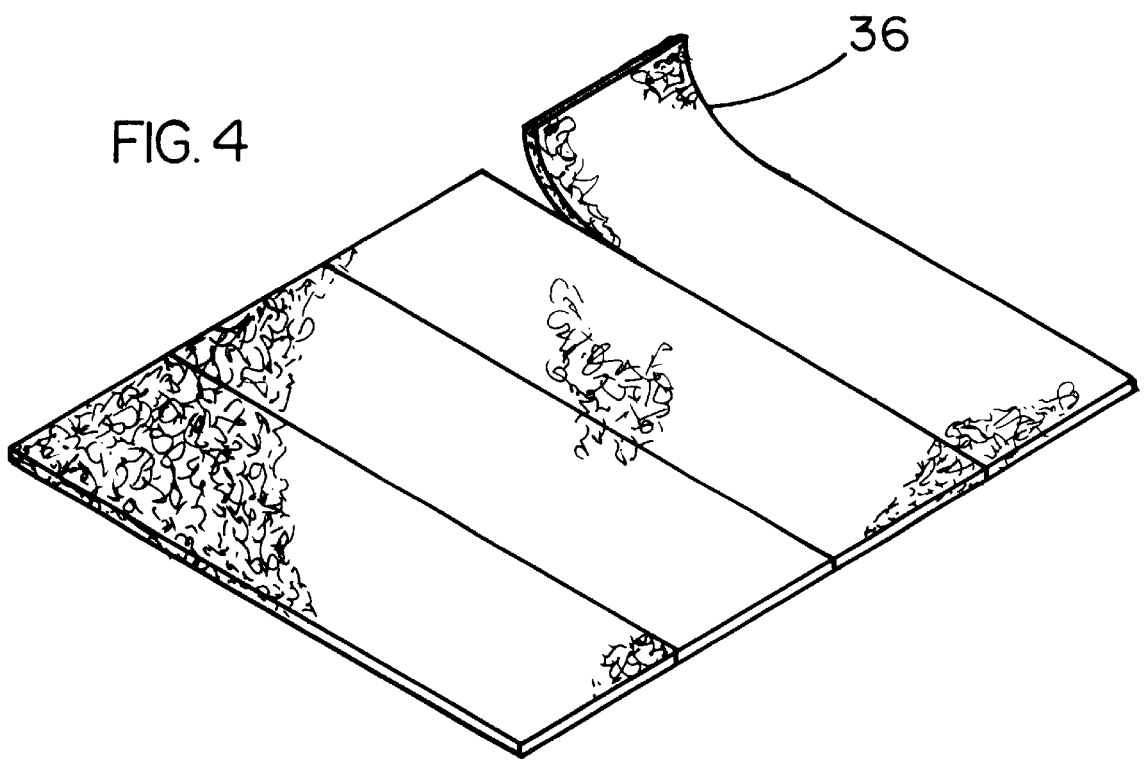
FIG. 4 is a schematic perspective view of the panels of the present invention.

With reference now to the drawings, and in particular to FIGS. 1 through 5 thereof, a new scent dispensing device for use in a clothes dryer embodying the principles and concepts of the present invention and generally designated by the reference numeral will be described.

As best illustrated in FIGS. 1 through 5, the scent dispensing device for use in a clothes dryer 10 generally comprises a cylinder 12. The cylinder 12 has a bottom wall 14. A peripheral wall 16 is integrally coupled to and extends upwardly from a peripheral edge of the bottom wall 14. The peripheral wall 16 has a plurality of apertures 18 therein.

A pair of annular ridges 20 are each integrally coupled to and extend around the peripheral wall 16. Each of the annular ridges 20 is generally nearer a top edge of the cylinder 12 than the bottom wall 14.

A cap member 22 has a top wall 24. A perimeter wall 26 is integrally coupled to and extends downwardly from the top wall 24. The perimeter wall 26 has an inner surface having a pair of annular depressions 28 therein. Each of the depressions 28 is adapted for releasably receiving one of the annular ridges 20.

A hook member 30 is preferably integrally coupled to an outer surface of the bottom wall 14. The hook member 30 comprises a base 32 and two leg members 34 extending away from the base. Each of the leg members 34 is integrally coupled to the bottom wall 14.

Each of a plurality of panels 36 comprises an absorbent material. The absorbent material preferably comprises a paper material. Cotton material is also envisioned.

In use, a scented fluid is positioned on the panels 36. The scented fluid may be any type of perfume or scented oil. The panel 36 is positioned in the cylinder 12 and placed in a clothes dryer with clothes. The apertures 18 allow the scent to travel through the peripheral wall while keeping the oil off of the clothes.

Figure 5:
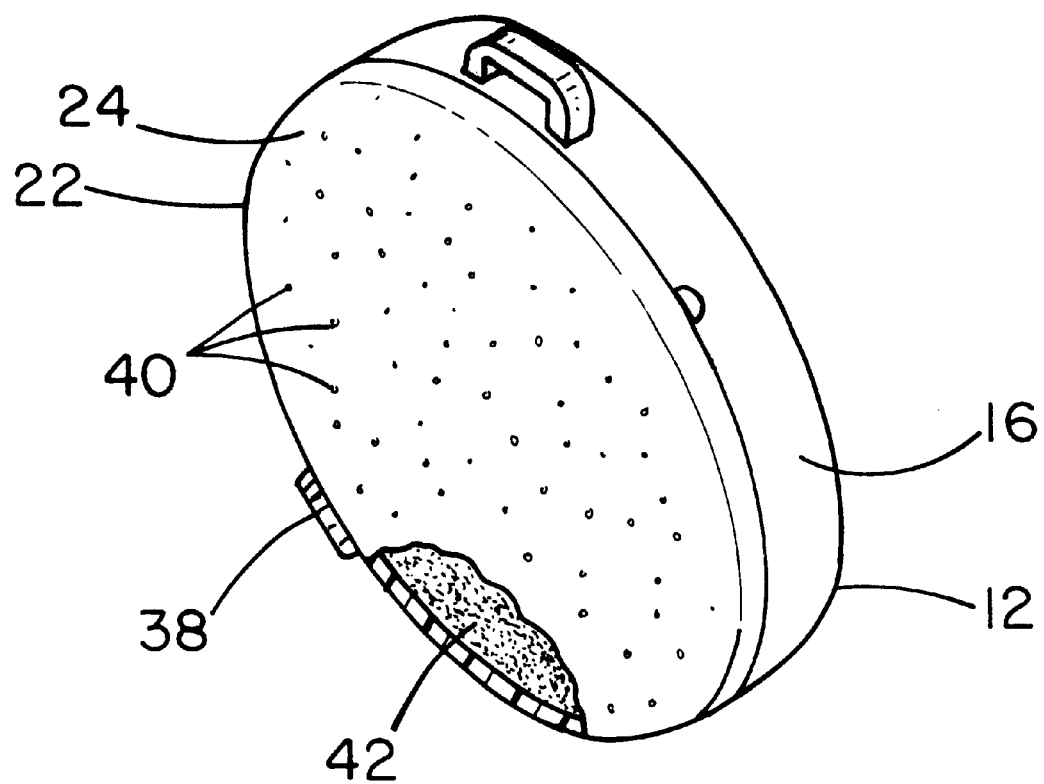
FIG. 5 is a schematic perspective view of the second embodiment of the present invention.

A second embodiment is shown in FIG. 5. It has a more compressed cylinder 12. The peripheral wall 16 does not have any apertures therethrough. A hinging means 38 hingedly couples the perimeter wall of the cap 22 to the peripheral wall. The top wall 24 has a plurality of apertures 40 therein. A plurality of absorbent granules 42 are positioned in the cylinder. The scented fluid is positioned on the absorbent granules. The second embodiment is then used in the same fashion as the first embodiment above.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scent dispensing device for placement in a clothes dryer, said device comprising:

a cylinder having a bottom wall, a peripheral wall being integrally coupled to and extending upwardly from a peripheral edge of said bottom wall, said peripheral wall having a plurality of apertures therein;

a cap member having a top wall, a perimeter wall being integrally coupled to and extending downwardly from said top wall for positioning over a top edge of said cylinder;

a plurality of panels, each of said panels comprising an absorbent material; and a scented fluid being selectively positioned on each of said panels, wherein one of said panels is positioned in said cylinder.

2. The scent dispensing device as in claim 1, further comprising:
- a pair of annular ridges being integrally coupled to and extending around said peripheral wall, each of said annular ridges being generally nearer a top edge of said cylinder than said bottom wall;
- said perimeter wall having an inner surface having a pair of annular depressions therein, each of said depressions being adapted for releasably receiving one of said annular ridges.

3. The scent dispensing device as in claim 1, further comprising:
- a hook member being integrally coupled to an outer surface of said bottom wall.

4. A scent dispensing device for placement in a clothes dryer, said device comprising:
- a housing having an interior, said housing having a base wall and a peripheral wall attached to and extending away from said base wall to define said interior, an upper edge of said peripheral wall defining an opening into said interior;
- a cover for covering said opening to said interior of said housing, said cover comprising a top wall having a lip for abutting said upper edge of said peripheral wall of said housing, said top wall having a plurality of apertures extending therethrough such that said interior of said housing is in fluid communication with an exterior of said housing through said apertures when said cover is closed over said opening;
- a hinge member being coupled to a first side of said housing and said cover such that said housing and said cover are hingably coupled together;
- a recess being formed on an outer surface of said peripheral wall on a second side of said housing for allowing access to a bottom edge of said lip of said cover for facilitating fingernail insertion between said cover and said housing when coupled together to lift said cover;
- a plurality of absorbent granules being positionable in said interior of said housing, a size of said granules being generally larger than a size of each of said apertures such that said granules are restricted from passing through said plurality of apertures;
- a scented fluid being positioned on each of said granules when said cover is rotated away from said housing exposing said granules; and
- wherein said scented fluid is readily released from each of said granules through each of said apertures when positioned in said housing and said opening is covered.

5. A scent dispensing device for placement in a clothes dryer, said device comprising:
- a cylinder having a bottom wall, a peripheral wall being integrally coupled to and extending upwardly from a peripheral edge of said bottom wall, said peripheral wall having a plurality of apertures therein;
- a pair of annular ridges being integrally coupled to and extending around said peripheral wall, each of said annular ridges being generally nearer a top edge of said cylinder than said bottom wall;
- a cap member having a top wall, a perimeter wall being integrally coupled to and extending downwardly from said top wall, said perimeter wall having an inner surface having a pair of annular depressions therein, each of said depressions being adapted for releasably receiving one of said annular ridges;
- a hook member being integrally coupled to an outer surface of said bottom wall, said hook member comprising a base and two leg members extending away from said base, each of said leg members being integrally coupled to said bottom wall;
- a plurality of panels, each of said panels comprising an absorbent material, said absorbent material comprising a paper material; and
- a scented fluid being positioned on said panels, wherein one of said panels is positioned in said cylinder.

* * * * *